(12) United States Patent
Mattes et al.

(10) Patent No.: US 11,369,257 B2
(45) Date of Patent: Jun. 28, 2022

(54) ENDOSCOPE

(71) Applicant: Henke-Sass, Wolf GmbH, Tuttlingen (DE)

(72) Inventors: Andreas Mattes, Duerbheim (DE); Sabine Pauli, Seitingen-Oberflacht (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 199 days.

(21) Appl. No.: 16/699,584

(22) Filed: Nov. 30, 2019

(65) Prior Publication Data
US 2020/0170486 A1 Jun. 4, 2020

(30) Foreign Application Priority Data
Nov. 30, 2018 (DE) .......................... 102018130553.2

(51) Int. Cl.
*A61B 1/005* (2006.01)
*A61B 1/05* (2006.01)
*A61B 1/00* (2006.01)

(52) U.S. Cl.
CPC ............ *A61B 1/05* (2013.01); *A61B 1/00013* (2013.01); *A61B 1/0052* (2013.01); *A61B 1/00121* (2013.01); *A61B 1/00137* (2013.01); *A61B 1/0057* (2013.01)

(58) Field of Classification Search
CPC ............ A61B 1/00064; A61B 1/00066; A61B 1/00105; A61B 1/0011; A61B 1/00121; A61B 1/00188; A61B 1/045; A61B 1/005; A61B 1/00137; A61B 1/00096; A61B 1/00098; A61B 1/00101; A61B 1/05; A61B 1/0052

USPC ....... 600/104, 131, 137, 174, 106, 147, 167, 600/146, 149
See application file for complete search history.

(56) References Cited

U.S. PATENT DOCUMENTS

| 4,323,304 A | 4/1982 | Ishii |
| 4,969,450 A | 11/1990 | Chinnock et al. |
| 5,808,813 A * | 9/1998 | Lucey ................ G02B 23/2438 348/65 |
| 6,436,108 B1 * | 8/2002 | Mears .............. A61B 17/12013 606/139 |
| 2003/0009084 A1 | 1/2003 | May et al. |
| 2004/0147809 A1 | 7/2004 | Kazakevich |

(Continued)

FOREIGN PATENT DOCUMENTS

| DE | 102012220621 A1 | 5/2013 |
| DE | 102012220651 A1 | 5/2014 |

*Primary Examiner* — Timothy J Neal
*Assistant Examiner* — Pamela F Wu
(74) *Attorney, Agent, or Firm* — Skaar Ulbrich Macari, P.A.

(57) ABSTRACT

An endoscope having an endoscope shaft and a main body, which is connected to the endoscope shaft and on which a first dial that has a first contact surface is mounted in a rotatable manner, is provided. The main body has a second contact surface against which the first contact surface bears. The contact surfaces move against one another when the first dial is rotated. A first setting unit is provided, using which a pressure force with which the first contact surface is pressed against the second contact surface is settable in order to set a minimum torque that is necessary in order to rotate the first dial.

17 Claims, 7 Drawing Sheets

(56) References Cited

U.S. PATENT DOCUMENTS

| | | | |
|---|---|---|---|
| 2007/0255104 A1* | 11/2007 | Maruyama | A61B 1/0052 600/148 |
| 2013/0342906 A1* | 12/2013 | Dahmen | G02B 27/0006 359/513 |
| 2014/0275763 A1 | 9/2014 | King et al. | |
| 2014/0371534 A1 | 12/2014 | Okamoto | |
| 2015/0112141 A1 | 4/2015 | Oginski et al. | |
| 2017/0347861 A1 | 12/2017 | Deutschendorf et al. | |
| 2019/0150714 A1 | 5/2019 | Onishi et al. | |

\* cited by examiner

Fig. 19

ENDOSCOPE

PRIORITY

This application claims the benefit of German Patent Application No. 10 2018 130 553.2, filed Nov. 30, 2018, which is hereby incorporated herein by reference in its entirety.

FIELD

The present invention relates to an endoscope having an endoscope shaft and a main body, which is connected to the endoscope shaft and on which a first dial is mounted in a rotatable manner.

BACKGROUND

Rotatable dials are provided on endoscopes for example in order, by means of the rotary position, to set a focusing position of a focusing optical unit or to rotate a camera connected to the dial for conjoint rotation. In order to rotate the dial, a certain minimum torque has to be applied. In order to produce an endoscope such that a desired minimum torque is set, very high tolerance requirements are placed on the components in question, resulting in complicated and expensive production.

SUMMARY

The disclosure includes an endoscope having an endoscope shaft and a main body, which is connected to the endoscope shaft and on which a first dial is mounted in a rotatable manner, in which the abovementioned difficulties are remedied as fully as possible.

An endoscope can have an endoscope shaft and a main body, which is connected to the endoscope shaft and on which a first dial that has a first contact surface is mounted in a rotatable manner. The main body can have a second contact surface against which the first contact surface bears, wherein the contact surfaces move against one another when the first dial is rotated. A first setting unit can be provided, using which a pressure force with which the first contact surface is pressed against the second contact surface is settable in order to set a minimum torque that is necessary in order to rotate the first dial.

Since the pressure force is settable by means of the first setting unit, the desired minimum torque can be set easily, for example during the assembly of the endoscope. Thus, it is possible to specify higher permissible tolerances for the individual components, and although these result in greater variations in the dimensions of the individual components, this can be compensated by the settable pressure force such that it is ultimately even possible to define the desired minimum torque with greater precision.

The first setting unit is configured in particular such that it cannot be actuated by a user in the assembled state of the endoscope. In other words, as soon as the endoscope has been assembled, adjustment by a user is not possible.

The first setting unit can have a first spring, the restoring force of which is settable.

The restoring force can be varied in particular by changing the length of the spring.

Thus, the first setting unit can have a first adjusting element, the axial position of which is variable, wherein varying the axial position of the first adjusting element changes the length of the first spring and as a result changes the restoring force of the first spring.

In particular, the first adjusting element can be connected to the main body via a first screw connection, which allows different screw-in depths. In particular, a fixing unit can be provided, which fixes a set screw-in depth.

The first spring can be in the form of a spiral spring. Furthermore, the first spring can be made of metal, and in particular of stainless steel.

The contact surfaces can be oriented transversely to a longitudinal direction of the endoscope shaft and the pressure force can act parallel to the longitudinal direction.

One of the contact surfaces can be a surface of a plastics plain bearing. The plastics plain bearing can be in particular in the form of a thrust washer.

The first dial can be axially displaceable in order to set the pressure force.

The second contact surface can be axially displaceable in order to set the pressure force.

The endoscope can have an optical channel, in which an optical unit that is displaceable in an axial direction is arranged. The first dial can thus be coupled to the optical unit such that when the first dial is rotated, the optical unit is moved axially. The coupling can be effected for example via magnets.

The first dial can have a connection to which a camera or optical coupler is mechanically fastenable for conjoint rotation, such that a rotation of the first dial brings about a rotation of the camera or optical coupler.

The endoscope according can have a second dial, which has a third contact surface and is mounted on the main body in a rotatable manner, wherein the main body has a fourth contact surface, against which the third contact surface bears. The third and fourth contact surfaces move against one another when the second dial is rotated, and a second setting unit is provided, using which the pressure force with which the third contact surface is pressed against the fourth contact surface is settable in order to set a minimum torque that is necessary in order to rotate the second dial.

The endoscope according to certain embodiments therefore comprises two dials, which can be rotated independently of one another and for which the minimum torque that is necessary in order to effect rotation can be set independently of one another. The second dial can be configured and developed in the same way as the first dial.

In particular, it is possible for the first dial to be coupled to the optical unit arranged in an optical channel such that when the first dial is rotated, the optical unit is moved axially. This axial movement can serve for example for focusing. The second dial can have a connection, to which a camera or optical coupler is mechanically fastenable for conjoint rotation. Thus, a rotation by means of the second dial can bring about a rotation of the camera or optical coupler.

The endoscope can have an objective and a transmission optical unit in the endoscope shaft. Using the objective and the transmission optical unit, an object located in front of the distal end of the endoscope can be imaged and transmitted to the proximal end of the endoscope.

The endoscope can be in the form of a straight-view endoscope (viewing direction corresponds to the longitudinal axis of the endoscope shaft) or of an oblique-view endoscope (viewing direction is at an angle other than 0° to the longitudinal axis of the endoscope shaft). The endoscope shaft can be rigid or flexible. The endoscope can be configured such that the objective and the transmission optical unit are hermetically sealed off from the environment. In particular, the endoscope can be autoclavable.

The endoscope can be in the form of a technical endoscope or in particular of a medical endoscope.

A plastics seal can be arranged between a first sealing surface of the first dial or of a first component connected to the first dial for conjoint rotation and a second sealing surface of the main body or of a second component connected to the main body for conjoint rotation, wherein a thermoplastic is used as plastic. In this way, not only can good sealing be achieved, but also an undesired stick-slip effect can be avoided.

The plastics seal can be in the form of an annular (for example circular-ring-shaped) seal with an integrated preloading element. In particular, the annular seal can be in the form of a grooved ring. The preloading element can be in the form of a steel spring or of a stainless steel spring. In particular a polyhaloolefin and particularly preferably polytetrafluoroethylene can be used as the plastic for the plastics seal.

A further plastics seal can be arranged between a third sealing surface of the first dial or of a third component connected to the first dial for conjoint rotation and a fourth sealing surface of the main body or of a fourth component connected to the main body for conjoint rotation, wherein a thermoplastic is used as plastic.

The third component can correspond to the first component or be a separate component. The fourth component can correspond to the second component or be a separate component.

The further plastics seal can be in the form of an annular (for example circular-ring-shaped) seal with an integrated preloading element. In particular, the annular seal can be in the form of a grooved ring. The preloading element can be in the form of a steel spring or of a stainless steel spring.

In particular a polyhaloolefin and particularly preferably polytetrafluoroethylene can be used as the plastic for the further plastics seal.

The endoscope can thus have one, two or more plastics seals, which are made of a thermoplastic and in particular of polyhaloolefin and particularly preferably of polytetrafluoroethylene and which are in the form for example of annular (for example circular-ring-shaped) seals (for example of grooved rings) with an integrated preloading element (for example a steel spring or a stainless steel spring).

The features mentioned above and those yet to be explained below are usable not only in the combinations specified but also in other combinations or on their own, without departing from the scope of the present invention.

In the following text, the invention is explained in more detail on the basis of exemplary embodiments with reference to the appended drawings, which likewise disclose features that are essential to the invention. These exemplary embodiments serve merely for illustration and should not be interpreted as limiting. For example, a description of an exemplary embodiment having a large number of elements or components should not be interpreted as meaning that all of these elements or components are necessary for implementation. Rather, other exemplary embodiments can also contain alternative elements and components, fewer elements or components, or additional elements or components. Elements or components of different exemplary embodiments can be combined with one another, unless specified otherwise. Modifications and alterations that are described for one of the exemplary embodiments can also be applicable to other exemplary embodiments. In order to avoid repetitions, identical or mutually corresponding elements in different figures are provided with the same reference signs and not explained several times.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

The invention is explained in yet more detail below with the aid of embodiment examples with reference to the attached drawings, which also disclose features essential to the invention. These embodiment examples merely serve the purpose of illustration and are not to be interpreted as limiting. For example, a description of an embodiment example with a plurality of elements or components is not to be interpreted to the effect that all of these elements or components are necessary for the implementation. Rather, other embodiment examples can also contain alternative elements and components, fewer elements or components or additional elements or components.

Elements or components of different embodiment examples can be combined with each other, unless otherwise indicated. Modifications and alterations which are described for one of the embodiment examples can also be applicable to other embodiment examples. To avoid repetitions, the same or corresponding elements are given the same reference numbers in different figures and are not explained repeatedly.

Figure 1:
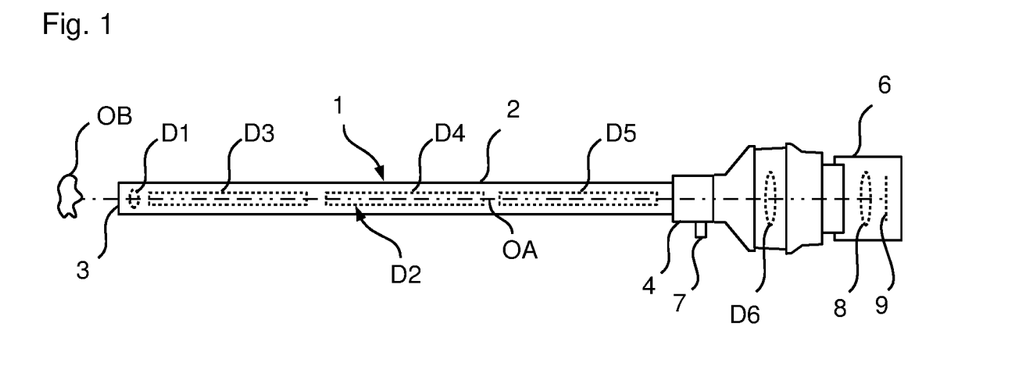
FIG. 1 shows a schematic illustration of an endoscope according to certain embodiments of the invention.
Figure 2:
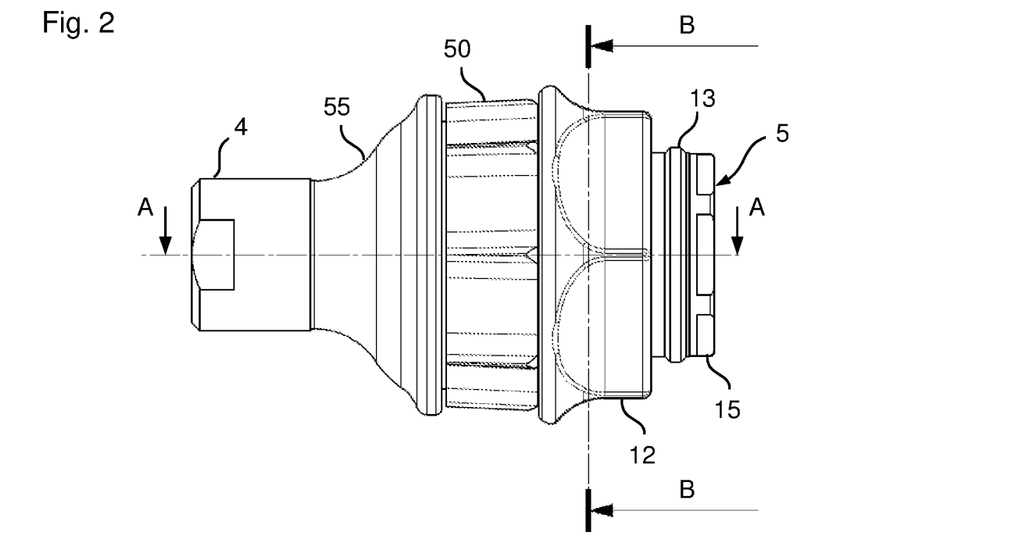
FIG. 2 shows an enlarged illustration of the main body of the endoscope in FIG. 1.

In the exemplary embodiment shown in FIGS. 1 and 2, the endoscope 1 comprises an endoscope shaft 2 having a distal end 3, which at the same time is the distal end of the endoscope 1. The end of the endoscope shaft 2 that is remote from the distal end 3 is connected to a main body 4 of the endoscope 1, which has an optical-unit connection 5 (which may comprise for example a C-mount connection 13 or a bayonet connection) for an optical recording device 6 (for example a video camera) or an optical coupling device. Furthermore, the main body 4 comprises an illumination light connection 7. The optical recording device 6, which contains for example an optical unit 8 and a CMOS sensor 9, is indicated only schematically in the illustration in FIG. 1 and can, but does not have to, be part of the endoscope 1.

The endoscope 1 can have, in the endoscope shaft 2, at its distal end 3, an objective D1, behind which a transmission optical unit D2 is arranged, which may comprise for example three rod lenses D3, D4 and D5. A further optical unit D6, which may be in the form for example of a focusing optical unit D6, can be arranged in the main body 4. Also indicated in FIG. 1 is an optical axis OA of the optical unit D1-D6, which extends parallel to the longitudinal direction of the shaft 2.

Thus, it is possible, in a known manner, to image an object OB located in front of the distal end 3 by means of the objective D1, the transmission optical unit D2 and the optical unit D6 to the proximal end of the endoscope 1. The imaging can take place to infinity or into a focusing plane that can be located inside or outside the endoscope 1. In the exemplary embodiment shown in FIG. 1, the imaging has been selected such that, by means of the recording device 6, the desired imaging can take place on the CMOS sensor 9, with the result that a digital recording of the image is possible.

Figure 3:
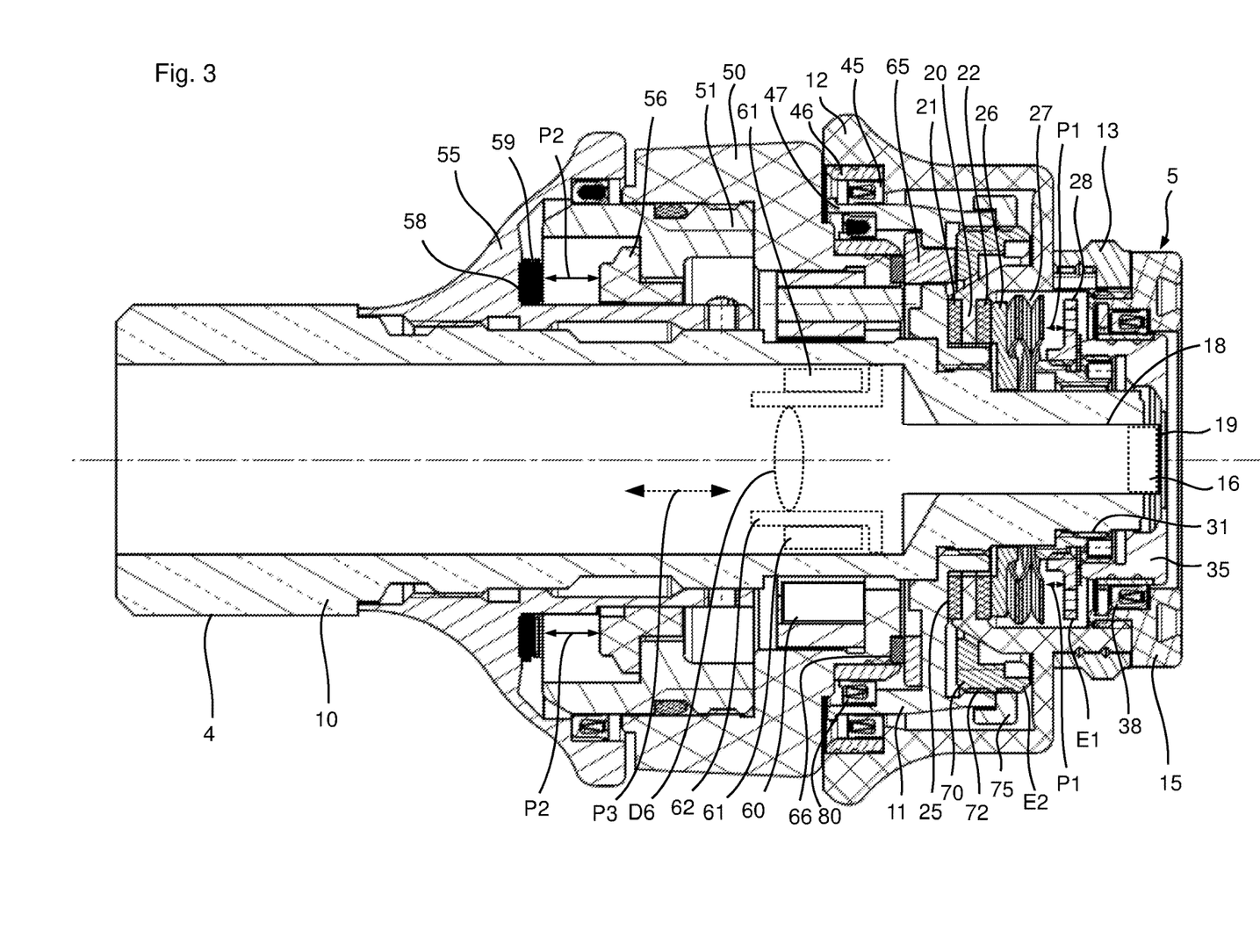
FIG. 3 shows a longitudinal section A-A through the main body in FIG. 2.

As is apparent in particular in FIG. 3, the optical-unit connection 5 is mounted so as to be rotatable with respect to a basic body 10 of the main body 4, wherein the necessary torque for rotating the optical-unit connection 5 is settable. This setting is carried out preferably during the assembly of the endoscope 1.

Figure 4:
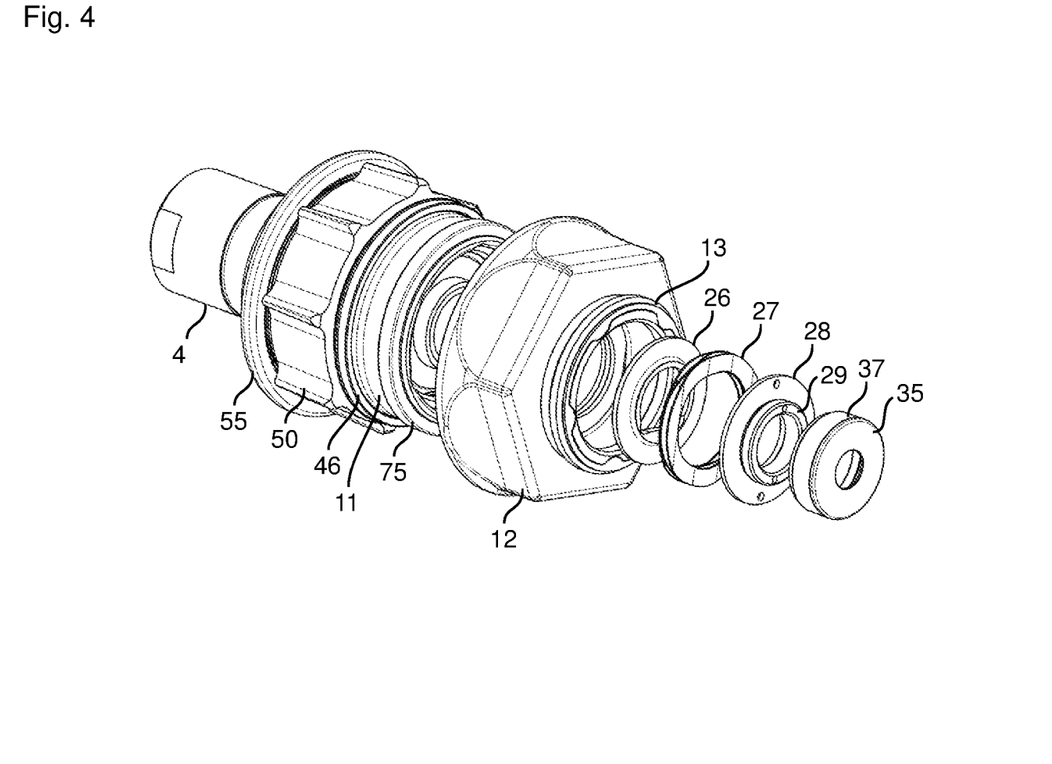
FIG. 4 shows a perspective exploded illustration of the main body, wherein a proximal terminal element is not illustrated in FIG. 4.
Figure 5:
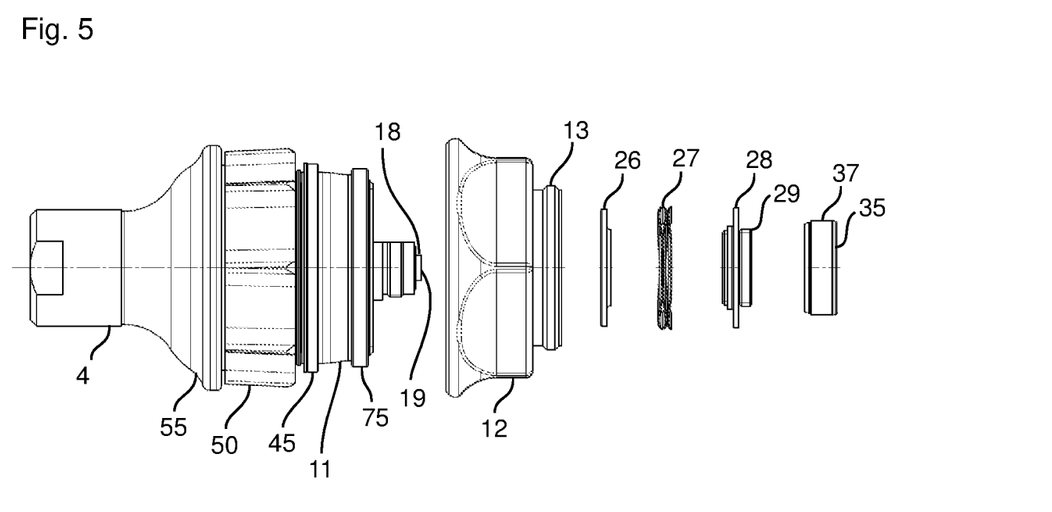
FIG. 5 shows an exploded illustration as per FIG. 4 in side view.
Figure 6:
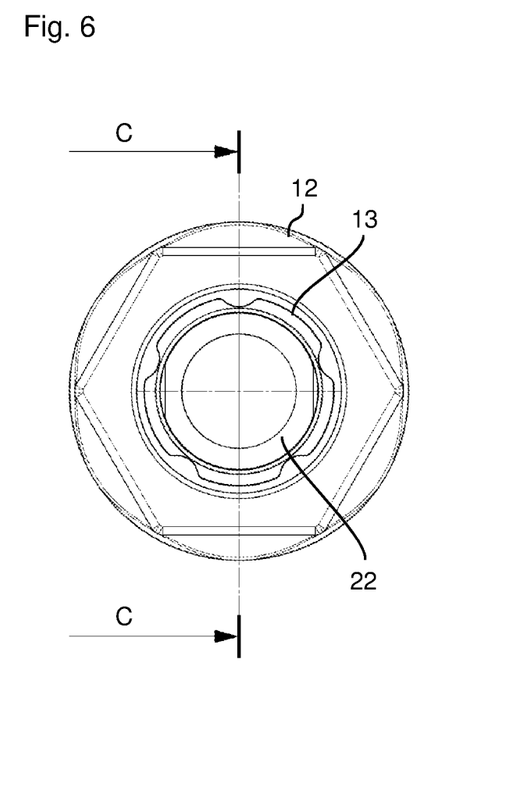
FIGS. 6 and 7 show a plan view and a sectional view C-C of the dial of the optical-unit connection.
Figure 7:
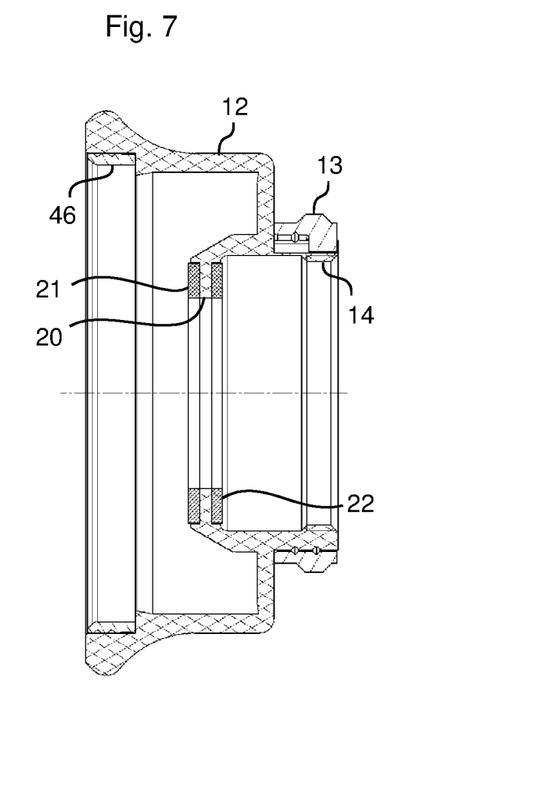
Figure 8:
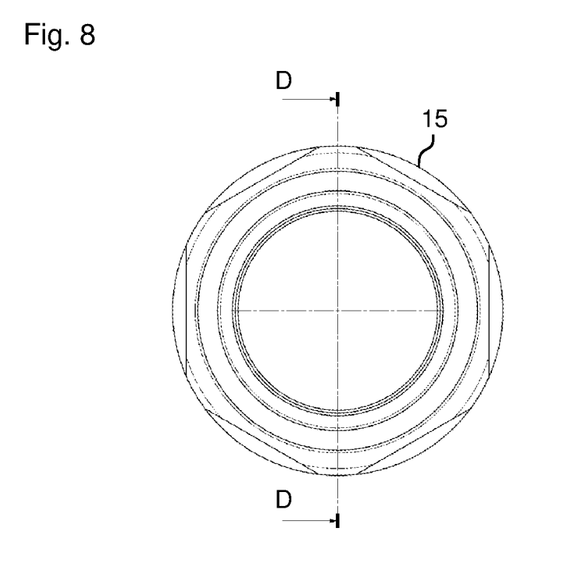
FIGS. 8 and 9 show a plan view and a sectional view D-D of the proximal terminal element of the optical-unit connection.

To this end, the endoscope 1 has a coupler bearing 11 (which is also illustrated in FIGS. 4 and 5), which is connected to the basic body 10 for conjoint rotation and with respect to which a connection dial 12 is mounted in a rotatable manner. At its proximal end, the connection dial 12 has a receiving thread 13 (which is in the form of an external thread), onto which the recording device 6 can be screwed. Furthermore, the connection dial 12 comprises at its proximal end an internal thread 14 (FIG. 7), into which a proximal terminal element 15 (FIGS. 8 and 9) is able to be screwed, the latter thus forming the proximal end of the endoscope 1. Through the proximal terminal element 15, light for making for example desired recordings of the endoscopic observations can pass. To this end, the endoscope 1 has an optical channel 18, the proximal end 19 of which is visible for example in FIG. 5. The proximal end of the optical channel 18 can be hermetically sealed by a proximal glass cover 16 (FIG. 3). For screwing into the internal thread 14, the proximal terminal element 15 has a corresponding external thread 17. Of course, the distal end of the optical channel 18 can also be hermetically sealed, such that the objective D1, the transmission optical unit D2 and the further optical unit D6 are isolated from the environment in an airtight manner.

The connection dial 12 also comprises an inner ring portion 20 (FIG. 7), on the two sides of which a distal connection plain bearing 21 and a proximal connection plain bearing 22 are arranged. The plain bearings 21, 22 can be in the form of plastics plain bearings and in particular in the form of polymer plain bearings. In particular, they can be realized as thrust washers.

In the assembled state, the distal connection plain bearing 21 bears against a first annular contact surface 25 of the coupler bearing 11. Against the proximal connection plain bearing 22 there presses a connection pressure disc 26, which is pressed by a connection spring 27 in the direction of the proximal connection plain bearing 22. To this end, the connection spring 27 bears with its other end against a connection adjusting disc 28, as is indicated by the double arrow P1 in FIG. 3. Only a part of the connection spring 27 is illustrated in FIG. 3.

Figure 10:
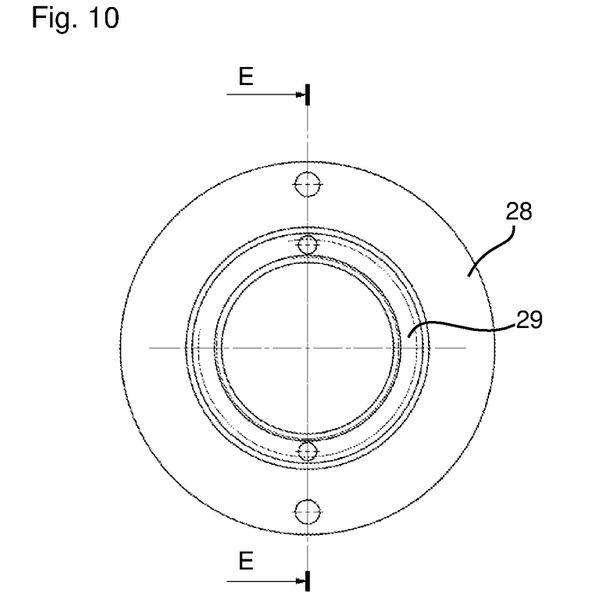
FIGS. 10 and 11 show a plan view and a sectional view E-E of the connection adjusting disc and of the connection threaded bush.

The connection adjusting disc 28 is connected to a connection threaded bush 29 (FIGS. 10 and 11), which has an internal thread 30 with which it is able to be screwed onto a corresponding external thread 31 of the basic body 10. Depending on how far the connection threaded bush 29 is screwed on, the distance between the connection adjusting disc 28 and the connection pressure disc 26, and thus the force with which the connection spring 27 presses against the proximal connection plain bearing 22, is changed and can thus be set. In this way, it is possible to define the desired torque that is necessary in order to rotate the connection dial 12 together with the external thread 13 and the screwed-on proximal terminal element 15.

The connection adjusting disc 28, the connection threaded bush 29, the connection pressure disc 26, and the connection spring 27 can be denoted setting unit E1, since they can be used to set the pressure force with which the connection pressure disc 26 is pressed against the proximal connection plain bearing 22.

Figure 11:
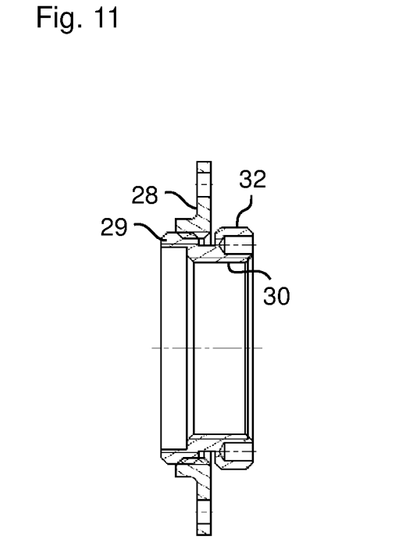
Figure 12:
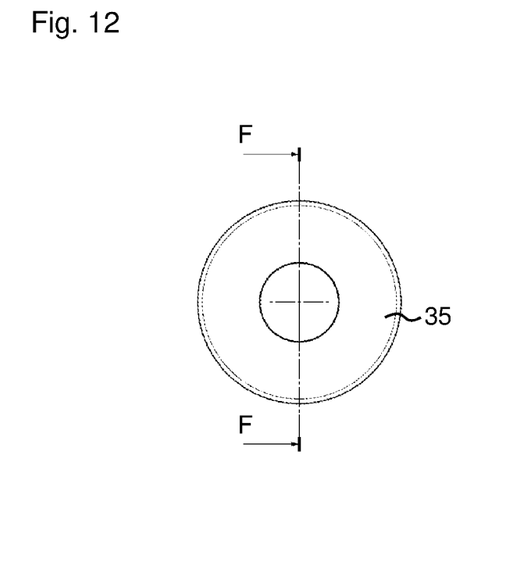
FIGS. 12 and 13 show a plan view and a sectional view F-F of the plastics cover.
Figure 13:
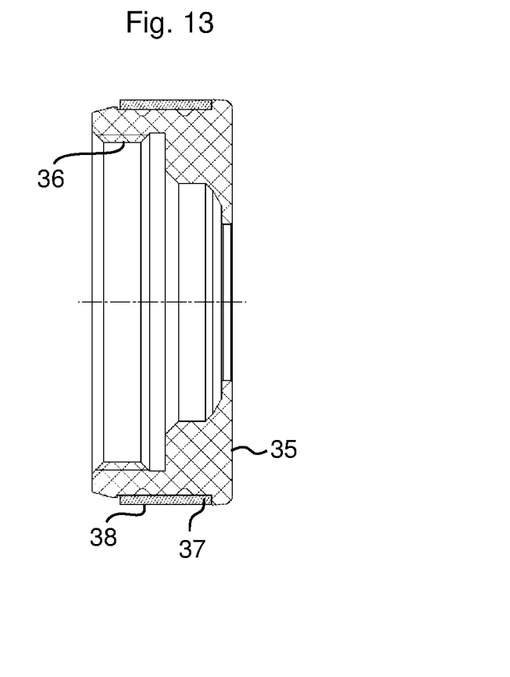

As can be gathered from FIG. 11, the connection threaded bush 29 has an external thread 32, onto which a plastics cover 35 (FIGS. 12 and 13) is able to be screwed with its internal thread 36. The plastics cover 35 has on its outer side a connection sliding bush 37. The connection sliding bush 37 can be made of steel and in particular of hardened steel. Its outer surface 38 can be polished.

Figure 9:
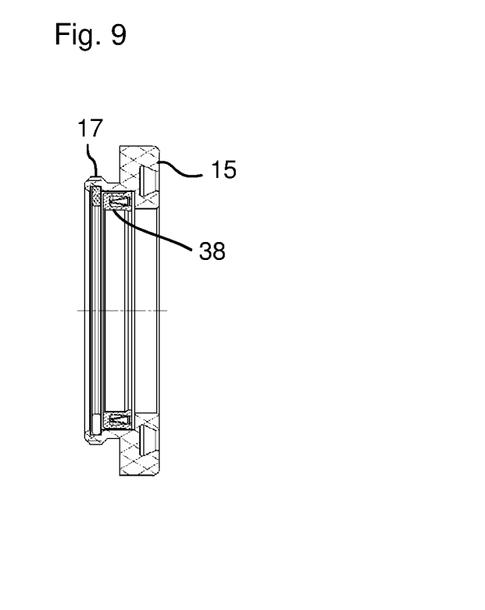
Figure 14:
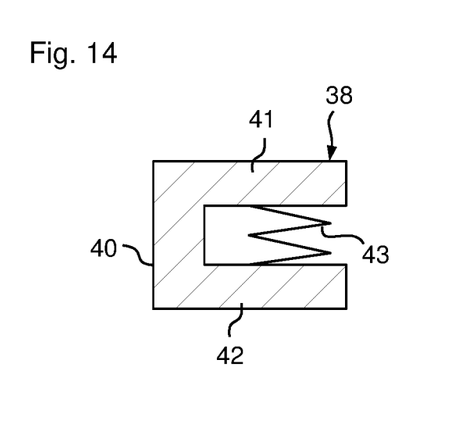
FIG. 14 shows a schematic sectional view of the profile of the first annular seal.
Figure 15:
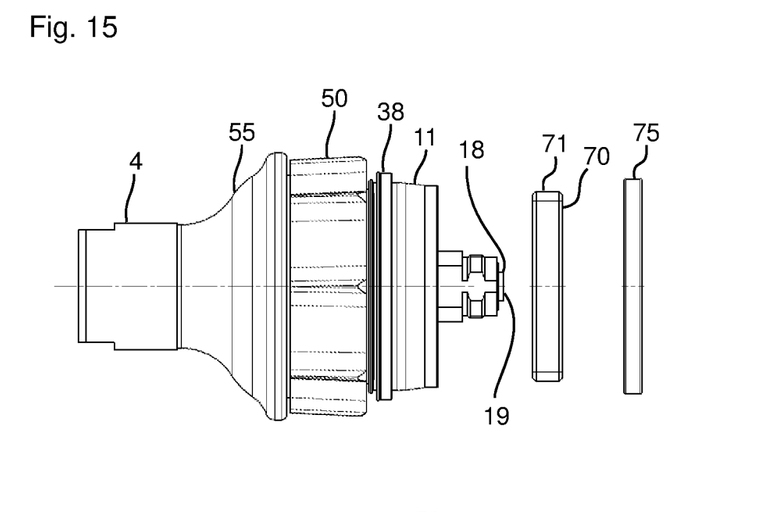
FIG. 15 shows an exploded illustration of a part of the main body in order to explain the setting of the minimum torque for the focusing dial.

Arranged between the connection sliding bush 37 and the proximal terminal element 15 is a first annular seal 38, which is shown in FIG. 9 and FIG. 3. The first annular seal 38 can be in particular a plastics seal. As plastic, it is possible to use in particular a thermoplastic, for example a polyhaloolefin. Particularly preferably, polytetrafluoroethylene (which is also frequently known as PTFE or Teflon) is used. In particular, the first annular seal 38 is in the form of a plastics grooved ring with an integrated spring (for example stainless steel spring) as preloading element. In this case, the plastics grooved ring 39 can have for example a C-shaped profile 40 with two free legs 41 and 42, which are preloaded outwards by a spring 43 (FIG. 14).

The use of a thermoplastic as plastic and in particular of PTFE results in the advantage that sufficient sealing with at the same time very little friction can be achieved. In this way, it is possible to reduce the undesired influence of the friction of such a seal on the torque required for rotating the connection dial 12. In particular, the undesired stick-slip effect is reduced or avoided, and so undesired sliding back no longer arises. A second annular seal 45 (FIGS. 3-5 and 7) is arranged between an annular inner portion 46 of the connection dial 12 and an annular outer portion 47 of the coupler bearing 11. The second annular seal 45 can be formed in an identical manner to the first annular seal 38.

Figure 18:
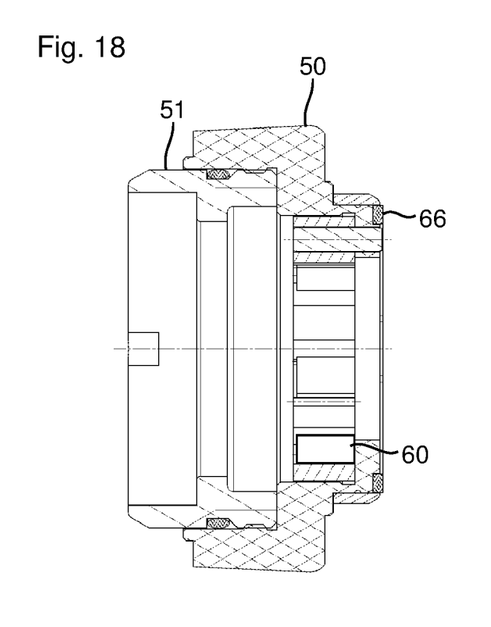
FIGS. 18 and 19 show a sectional view G-G and a plan view of the focusing dial together with the focusing sliding bush.
Figure 19:
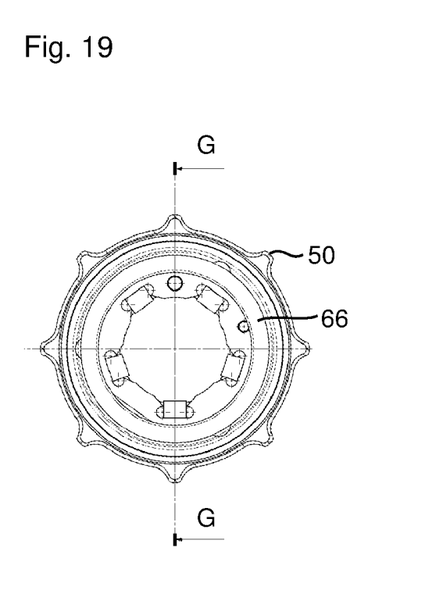

Also provided is a focusing dial 50, which is connected to a focusing sliding bush 51 for conjoint rotation (FIGS. 3, 18 and 19). Fastened to the basic body 10 for conjoint rotation is a rotor stop 55, which supports a bearing bush 56 such that it is displaceable only axially. Arranged between a distal end of the bearing bush 56 and a stop 58 of the rotor stop 55 is a focusing spring 59, which subjects the bearing bush 56 to a force in the direction of the proximal end of the endoscope, as is indicated by the double arrow P2. Only a part of the focusing spring 59 is illustrated in FIG. 3.

The distance between the bearing bush 56 and the stop 58 of the rotor stop 55 can, as described in detail below, be changed and set in order as a result to set the desired torque that is necessary in order to rotate the focusing dial 50. The focusing dial 50 bears one or more magnets 60, which interact with magnets 61 of an optical unit 62 such that rotation of the magnet 60 or magnets 60 has the result that this rotary movement is converted into an axial movement (double arrow P3) of the optical unit 62, as is illustrated schematically in FIG. 3. In this way, it is possible for example to carry out focusing.

Figure 16:
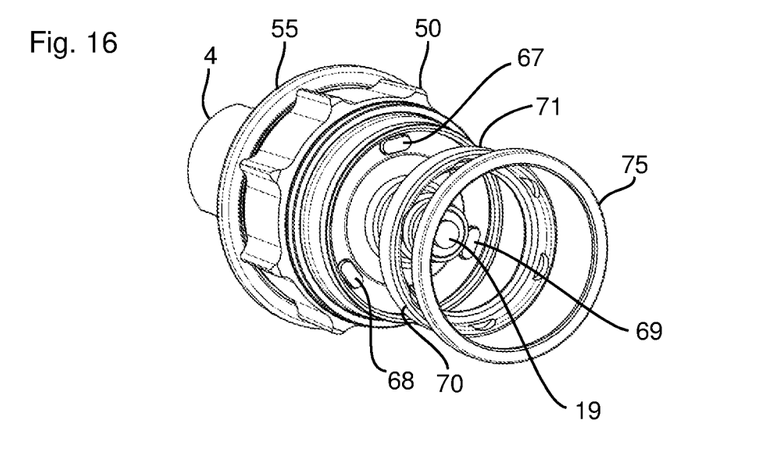
FIG. 16 shows the exploded illustration as per FIG. 15 in a perspective illustration.
Figure 17:
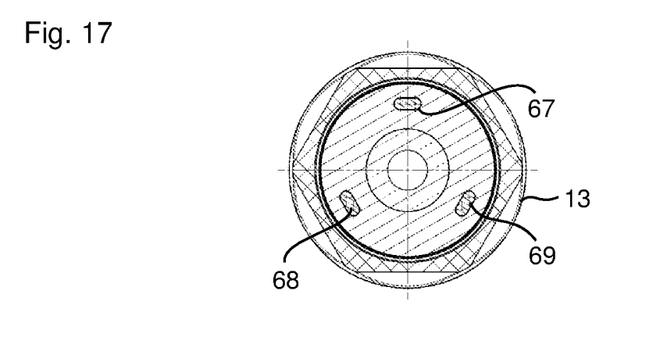
FIG. 17 shows the sectional view B-B from FIG. 2.

A focusing pressure disc 65 is guided axially in the coupler bearing 11 and at the same time prevented from rotating, which presses against a proximal focusing plain bearing 66 of the focusing dial 50. The proximal focusing plain bearing 66 can be configured in an identical manner to the distal connection plain bearing 21. The guiding of the focusing pressure disc 65 in the coupler bearing 11 can be realized for example by three axially extending protrusions 67, 68, 69 (FIGS. 3, 16 and 17), which extend through corresponding through-openings in the coupler bearing 11. The protrusions 67 to 69 can be spaced apart from one another for example by 120° in the circumferential direction, as is indicated in FIGS. 16 and 17.

A focusing adjusting disc 70 screwed into the coupler bearing 11 presses on the protrusions 67 to 69. To this end, the focusing adjusting disc 70 has an external thread 71, which is screwed into a corresponding internal thread 72 of the coupler bearing 11. The further the focusing adjusting screw 70 is screwed in, the further the focusing pressure disc 65 is moved in the direction of the distal end of the endoscope 1. This movement results in axial displacement of the focusing dial 50 with the focusing sliding bush 51 and thus also of the bearing bush 56, such that the distance between the distal end of the bearing bush 56 and the stop 58 of the rotor stop 55 becomes smaller, with the result that the focusing spring 59 is more greatly compressed. This results in a higher restoring force and thus in a greater torque that is necessary in order to rotate the focusing dial 50. Screwed onto the external thread 71 of the focusing adjusting disc 70 is a focusing nut 75 having a corresponding internal thread 76, which fixes the set screw-in depth of the focusing adjusting disc 70.

The focusing pressure disc 65, the focusing adjusting disc 70 can, together with the focusing spring 59, be denoted setting unit E2, using which the force with which the focusing pressure disc presses against the proximal focusing plain bearing 66 can be set.

Arranged between the focusing dial 50 and the coupler bearing 11 is a third annular seal 80. Furthermore, a fourth annular seal 81 is arranged between the focusing sliding bush 51 and the rotor stop 55. The third and fourth annular seals 80, 81 can be configured in an identical manner to the first annular seal 38.

In the endoscope 1, it is thus possible to set the necessary torque for rotating the connection dial 12 and the focusing dial 50 independently of one another. As a result of the described possibility of individual setting of the torque to be exceeded, it is advantageously possible for the permissible tolerances of the individual components to be greater compared with previously known solutions, since the resultant greater variations in the dimensions of the individual components can be compensated by the described settability of the torques for the connection dial 12 and the focusing dial 50.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. An endoscope, comprising:
   an endoscope shaft; and
   a main body, which is connected to the endoscope shaft and on which a first dial that has a first contact surface is mounted in a rotatable manner,
   wherein the main body has a second contact surface against which the first contact surface bears, wherein the contact surfaces move against one another when the first dial is rotated, and
   wherein a first setting unit is provided, using which a pressure force with which the first contact surface is pressed against the second contact surface is settable in order to set a minimum torque that is necessary in order to rotate the first dial, and
   wherein the contact surfaces are oriented transversely to a longitudinal direction of the endoscope shaft and the pressure force acts parallel to the longitudinal direction.

2. The endoscope according to claim 1, wherein the first setting unit includes a first spring, a restoring force of which is variable in order to set the pressure force.

3. The endoscope according to claim 1, wherein the first setting unit includes a first adjusting element, the axial position of which is variable, and wherein varying the axial position of the first adjusting element changes the length of the first spring, and as a result, changes the restoring force of the first spring.

4. The endoscope according to claim 3, wherein the first adjusting element is connected to the main body via a first screw connection, which allows different screw-in depths.

5. The endoscope according to claim 1, wherein the first spring is in the form of a spiral spring.

6. The endoscope according to claim 1, wherein one of the contact surfaces is a surface of a plastic plain bearing.

7. The endoscope according to claim 6, wherein the plastic plain bearing is in the form of a thrust washer.

8. The endoscope according to claim 1, wherein the first dial is axially displaceable in order to set the pressure force.

9. The endoscope according to claim 1, wherein the second contact surface is axially displaceable in order to set the pressure force.

10. The endoscope according to claim 1, wherein the endoscope includes an optical channel, in which an optical unit that is displaceable in an axial direction is arranged, and wherein the first dial is coupled to the optical unit such that when the first dial is rotated, the optical unit is moved axially.

11. The endoscope according to claim 1, wherein the first dial includes a connection to which a camera or optical coupler is mechanically fastenable for conjoint rotation, such that a rotation of the first dial brings about a rotation of the camera or optical coupler.

12. The endoscope according to claim 1, further comprising:
a second dial, which comprises a third contact surface and is mounted on the main body in a rotatable manner,
wherein the main body comprises a fourth contact surface, against which the third contact surface bears,
wherein the third and fourth contact surfaces move against one another when the second dial is rotated, and
wherein a second setting unit is provided, using which a pressure force with which the third contact surface is pressed against the fourth contact surface is settable in order to set a minimum torque that is necessary in order to rotate the second dial.

13. The endoscope according to claim 1, wherein a plastic seal is arranged between a first sealing surface of the first dial or of a first component connected to the first dial for conjoint rotation and a second sealing surface of the main body or of a second component connected to the main body for conjoint rotation, wherein a thermoplastic is used as plastic.

14. The endoscope according to claim 13, wherein the plastic seal is in the form of an annular seal with an integrated preloading element.

15. The endoscope according to claim 14, wherein the annular seal is in the form of a grooved ring.

16. The endoscope according to claim 15, wherein the preloading element is in the form of a steel spring.

17. The endoscope according to claim 14, wherein the preloading element is in the form of a steel spring.

* * * * *